United States Patent [19]

Matsuno et al.

[11] Patent Number: 5,135,746
[45] Date of Patent: Aug. 4, 1992

[54] CONTROL OF PROTOZOAL DISEASE

[75] Inventors: Toshimi Matsuno, Osaka; Fumio Hariguchi, Kobe; Tsutomu Okamoto, Osaka, all of Japan

[73] Assignee: Takeda Chemical Industries, Ltd., Osaka, Japan

[21] Appl. No.: 513,945

[22] Filed: Apr. 24, 1990

[30] Foreign Application Priority Data

Apr. 25, 1989 [JP] Japan .................................. 1-106394

[51] Int. Cl.⁵ ..................... A61K 35/78; A61K 31/70; A61K 31/725; A61K 31/335
[52] U.S. Cl. .................................. 424/195.1; 514/25; 514/53; 514/450; 514/452; 514/456; 514/462; 514/738
[58] Field of Search ................. 424/195.1; 514/53, 25, 514/456, 738, 462, 452, 450

[56] References Cited

PUBLICATIONS

"The Merck Index", Pub. by Merck & Co. Inc. Tenth Edition (1983).
"Protozoan Populations of Reticulitermes-flavipes exposed to Heart Wood Blocks of 21 American Species". Mauldin et al., "Material und Organismen" Berlin 16(1), 1981, 15–28.
Chemical Patents Index, Documentation Abstracts Journal, B Section, 88-268226/38 (1988).
Chemical Patents Index, Documentation Abstracts Journal, B Section, 88-268232/38 (1988).
Central Patents Index, Basic Abstracts Journal, B Section 65555X/35 (1976).

*Primary Examiner*—John W. Rollins
*Attorney, Agent, or Firm*—Wenderoth, Lind & Ponack

[57] ABSTRACT

A method for prophylaxis or treatment of protozoal disease which comprises administering to domestic animal a plant component having antiprotozoal activity in combination with an ionophore antibiotic is disclosed. The method is safe and economical, and gives the excellent effect to protozoal disease, so that it is useful for the poultry and the live-stock industry.

15 Claims, No Drawings

CONTROL OF PROTOZOAL DISEASE

BACKGROUND OF THE INVENTION

The present invention relates to prophylactic and therapeutic agents for protozoal disease which comprise plant components having antiprotozoal activity in combination with ionophore antibiotics.

As diseases caused by protozoan parasites, there have been known various kinds of diseases such as avian coccidiosis, coccidiosis in poultry (for example, turkeys and quails), coccidiosis in swine, cattle, sheep and so on, avian leucocytozoon disease, toxoplasmosis, malaria, piroplasmosis, trypanosomiasis and leishmaniasis. As preventive therapeutic agents for such protozoal diseases, there have previously been used sulfa drugs, antithiamine drugs, quinoline derivatives, pyridinol derivatives, nucleic acid derivatives, quinazoline derivatives, guanidine derivatives, folate antagonists, ureal drugs, ionophore antibiotics and the like.

However, as observed in the prevention and treatment of avian coccidiosis, it has recently been revealed that protozoa in the field come to exhibit resistance against these antiprotozoal drugs [MacDougald et al., *Avian Diseases* 30, 690–694 (1986); Ikeda et al., *Collected Summaries of Lectures at* 103rd Meeting of Japanese Veterinary Society VI-1, 150 (1987)]. Further, some antiprotozoal drugs have a tendency to remain highly in the bodies of animals to which the drugs have been administered [*Drugs for Animals: Remaining of Feed Additives in Animal and Marine Products and Analytical Methods of the Same*, Research Institute for Animal Science Biochemistry and Toxicology (1985)]. This fact has been grasped as an important problem on the livestock industry.

On the other hand, it has recently been revealed that condensed tannins widely contained in higher plants and resin glycosides contained in the plants of the convolvulus family show biological activity to protozoa (Japanese Patent Unexamined Publication Nos. 63-196514/1988 and 63-196523/1988). In addition, plants such as *Polgala tenuifolia, Bupleurinum falcatum, Fagara ailanthoides, Uncaria kawakamii, Lycoris radiate* and *Anemarrhena asphodeloides*, and their components have been used for the treatment of diseases such as malaria and amebic dysentery from old times [Kariyone and Kimura, *Modern Japanese and Chinese Medicated Botany*, published on Sep. 10, 1959]. There have also been handed down *Verbena officinalis, Carpesium abratanoides, Artemisia annua* and *Dichloa febrifuga* as antimalarial drugs [Chen Zai Ren, *Iconographical Chinese Medicinal Dictionary*<*Chinese Pharmaceutical Dictionary*>, published by Kodansha on May 10, 1982]. However, there is a disadvantage for the application of these plants and their components to livestock animals, when it is considered that these are required to be used in substantial amounts on prescriptions and take a lot of labor for decoction and the like.

Avian coccidiosis, one of protozoal disease, is a disease whose symptom appears by that protozoan parasites of the genus Eimeria, such as mature oocysts of *Eimeria tenella, Eimeria necatrix, Eimeria acervulina, Eimeria maxima, Eimeria brunetti* and *Eimeria mivati*, are orally ingested in chickens, parasitized on digestive tracts and propagated. The chickens attacked with the disease excrete diarrheal feces, mucous feces, viscous bloody feces or blood, and lose their vitality and appetite, which cause poor growth, decreased body weight, reduced feed efficiency, reduced resistance against diseases and reduced egg-laying performance during egg-laying periods, and ultimately sometimes cause death. For this reason, this disease has been inflicting an enormous economic damage on the poultry raising industry.

Avian leucocytozoon disease is a disease whose symptom appears due to protozoa *Leucocytozoon caulleryi*. The chickens attacked with this disease show significant bleeding, hemolysis, harm of hemocytes and the like in their bodies, and therefore exhibit symptoms such as anemia and green feces, which lead to a decrease in body weight, poor growth and a reduction in egg laying, and further cause death. Thus, the damage suffered from this disease is serious.

As to coocidiosis in cattle, conditions suitable for infection are easily produced due to recent new raising methods of beef cattle. Raising cattle exhibit diarrhea, anemia, prostration and a poor appetite, which lead to poor growth.

As exemplified above, diseases caused by protozoa, particularly sporozoa, cause great damage to the livestock industry such as the cattle raising industry and the poultry raising industry including the chicken raising industry.

There is the disadvantage that sulfa drugs, quinoline derivatives, pyridinol derivatives, nucleic acid derivatives, quinazoline derivatives, diphenylurea derivatives, guanidine derivatives, dinitroimide derivatives, thiamine derivatives, folate antagonists, ionophore antibiotics and the like which have previously been used for the prophylaxis and treatment of such protozoal disease are expensive. In addition, these drugs are facing the serious problem that their original effect is difficult to be expected, because protozoa in the field reduced in sensitivity to the drugs are increasing.

On the other hand, as new ideas, attempts have recently been made to combine ionophore antibiotics particularly selected from the commercially available antiprotozoal drugs with other different kinds of antiprotozoal drugs, or other antibiotics such as mucilin, anthracycline and frenolicin. However, these themselves are strong bioactive substances, so that there is the fear of bioactive expression newly induced by combined administration and unfavorable to animals to which the combined drugs is administered, or of an increase in toxicity. It is therefore necessary to prove that there is not any such fear on practical use. Accordingly, these attempts have difficulty in their application.

SUMMARY OF THE INVENTION

In view of the above situation, we conducted intensive investigations to provide excellent prophylactic and therapeutic agents for protozoal disease, and consequently discovered that the combinations of ionophore antibiotics and plant components having antiprotozoal activity or plant bodies containing them cause the combined drugs to exhibit a synergistic effect, whereby protozoal disease can be depressed by dosage in practicable amounts. This discovery was followed by further investigations, which culminated in the completion of the present invention.

The present invention provides prophylactic and therapeutic agents for protozoal disease which comprise plant components having antiprotozoal activity in combination with ionophore antibiotics.

DESCRIPTION OF THE PREFERRED EMBODIMENTS

Examples of the plant components having antiprotozoal activity include condensed tannins, resin glycosides, magnolol and their derivatives.

The condensed tannins are a group of compounds having flavan-3-ol (catechin) as constituent units and forming trimers and further polymers by various bonding forms, as represented by the following formula (I):

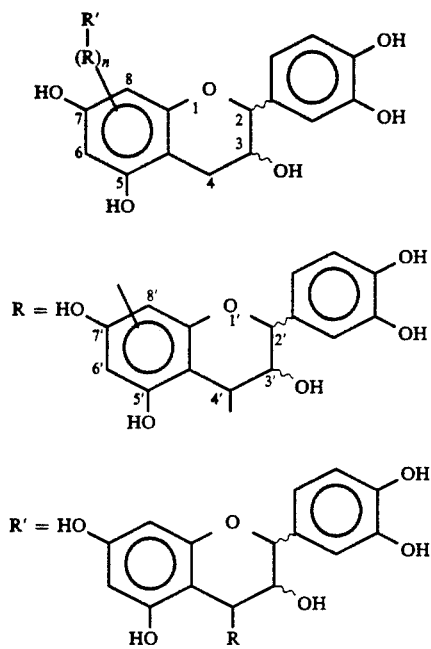

in which n is an integer of 1 to 15, the 4' position of R is bound to the 6 position or the 8 position of formula (I), R' is bound to the 6' position or the 8' position of R; and when n is an integer of 2 to 15, the 4' position of R is bound to the 6' position or the 8' position of R.

As the condensed tannins in the present invention, there may be used purified tannins, such as plants or crude drugs containing the condensed tannins. With respect to the plants, the whole plant or parts thereof (such as cortices, flowers, seeds, leaves, roots and stems) containing the condensed tannins are used in the raw, in the dried state, or in the form crushed or pulverized after drying. It is preferable to use fabricated products crushed or pulverized after drying.

Examples of the plants containing the condensed tannins used in the present invention include the plants of the camphor tree family such as *Cinnamomum camphora* S., *Cinnamomum Loureirii* N., *Machilus Thumnbergii* S., *Benzoin unbellatum* R., *Parabenzoin trilobum* N., *Lindera erythrocarpa* M.,*Lindera strychnifolia* F., *Lindera glauca* B., *Cinnamomum aponicum* S., *Cinnamomum dophnoides* S., *Laurus nobilis* L., *Parabenzoin praecox* N., *Cassytha filiformis* L., *Neolitsea sericea* B., *Lindera obtusiloba* B., *Neolitsea aciculata* B. and *Cinnamomum cassia* B.; the plants of the magnolia family such as *Illicium religiosum* S.; the plants of the smartweed family such as *Rheum palmatum* L., *Rheum tanguticum* and *Polygonum multiflorum* T.; the plants of the ephedra family such as *Ephedra equisetina* B. and *Ephedra distachya* L.; the plants of the palm family such as *Area catechu* L.; the plants of the azalea family such as *Vaccinium vitisidaea* L.; the plants of the myristica family such as *Myristica iragrans* H.; the plants of the myrica family such as *Myrica rubra* S.; the plants of the madder family such as *Uncaria gambir* R. and *Chinona ledgeriana* M.; the plants of the rose family such as *Rosa multiflora* T. and *Rhaphiolepis umbellata* M.; the plants of the water lily family such as *Nelumbo nucifera* G.; and a group of plants named generically as Mangrove, for example, the plants of the Rhizophoraceae family such as *Rhizophora mucronata* L., *Bruguiera cylindrica* B., *Bruguiera gymnorrhiza* L. and *Kandelia candele* L., the plants of the Lumnitzern family such as *Lumnitzern racemosa* W. and *Lumnitzern coccinea* W., the plants of the Sonnerrita family such as *Sonnerrita alba* Smith, and the plants of the Maliaceae family such as *Xylocarpus granatum* Koen. In particular, *Parabenzoin trilobum* N., *Neolitsea aciculata* B. and *Lindera obtusiloba* B. classified as the camphor tree family, and *Rhizophora mucuronata* L., *Bruguiera gymnorrhiza* L. and *Kandelia candele* L. classified as the bruguiera family are preferable, and *Parabenzoin trilobum* N., *Neolitsea aciculata* B., *Rhizophora mucronata* L. and *Kandelia candele* L. are more preferable.

The crude drugs containing the condensed tannins used in the present invention include the wholes or condensed tannin-containing parts of the above plants and their fabricated products, such as cassia, cinnamon, *Parabenzoin trilobum* bark, rhubark, *Polygonum multiflorum*, ephedra, *Areca catechu*, *Vaccinium vitis-idaea*, *Myristica iragrans*, myrica bark, Eijitu, catechu, cinchona bark, *Rhaphiolepis umbellata* bark, *Kandelia candele* bark, lotus receptacle, Cutch and Koozyuhi. In particular, cassia, rhubark, *Polygonum multiflorum*, catechu and Koozyuhi are preferable, and catechu and Koozyuhi are more preferable.

When the purified condensed tannins are used in the present invention, they can be produced, for example, by the following methods.

With respect to the plants and crude drugs described above, the whole plant or parts thereof (such as cortices, flowers, seeds, leaves, roots and stems) containing the condensed tannins, which are in the raw, in the dried state, or preferably in the form crushed or pulverized after drying, are extracted with about 5-fold to 10-fold amounts of sole or mixed solvents of alcohols such as methanol and ethanol, ketones such as acetone and methyl ethyl ketone, chloroform and the like, at room temperature or at elevated temperatures under reflux for 2 hours to 2 weeks. Extracted solutions are concentrated, and then subjected to column chromatography using polystyrene-series resins or dextran-series resins such as Diaion HP-20, Diaion XAD-2, MCI-Gel CHP-20 and Sephadex LH-20 to concentrate fractions eluted with hydrous alcohols or hydrous acetone, whereby the purified condensed tannins can be obtained.

Examples of the resin glycosides include pharbitin; jarapin; orizabin; Mb-1 (1)-, Mb-2 (2), Mb-3 (3), Mb-4 (4) and Mb-5 (5) represented by the following formula (II) [*Collected Summaries of Lectures at 27th Natural Organic Compound Discussion Meeting* 427–434 (1985)]; and Oc-1 (6), Oc-2 (7), Oc-3 (8), and Oc-4 (9) represented by the following formula (III) [the same as above]:

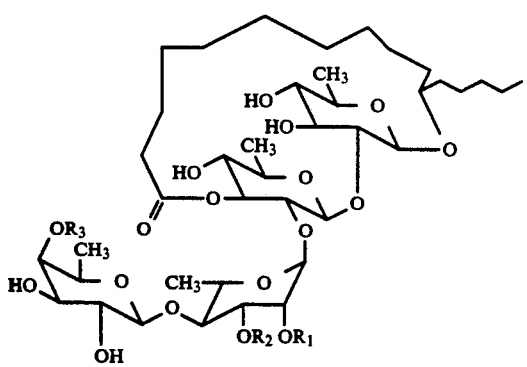
(II)

Mb-1 (1): $R_1$=H, $R_2$=mba, $R_3$=mba
Mb-2 (2): $R_1$=H, $R_2$=mba, $R_3$=iba
Mb-3 (3): $R_1$=mba, $R_2$=H, $R_3$=mba
Mb-4 (4): $R_1$=mba, $R_2$=H, $R_3$=iba
Mb-5 (5): $R_1$=mba, $R_2$=H, $R_3$=H

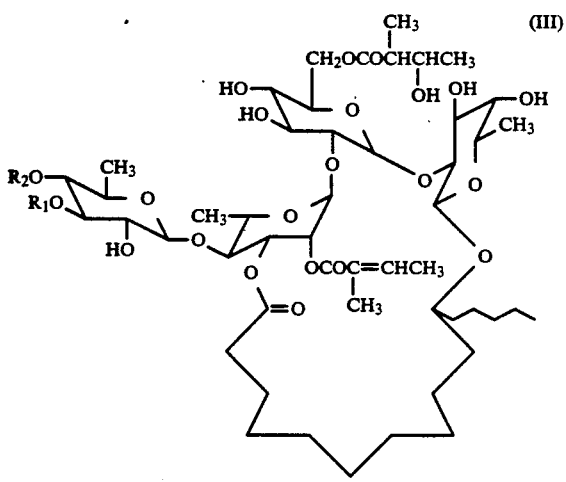
(III)

Oc-1 (6): $R_1$=iba, $R_2$=H
Oc-2 (7): $R_1$=H, $R_2$=mba
OC-3 (8): $R_1$=H, $R_2$=iba
Oc-4 (9): $R_1$=H, $R_2$=nla in which mba represents α-methylbutyric acid, iba represents isobutyric acid, and nla represents nilic acid.

As for the resin glycosides contained in the plants of the convolvulus family, there may be used purified resin glycosides, crude plant bodies containing the resin glycosides such as the wholes or parts (such as cortices, flowers, seeds leaves, roots and stems) of plants containing the resin glycosides, or preferably fabricated products (such as pharbitis seeds, orizaba jalap resins, jalap resins, pharbitis resins, orizaba jalap roots and jalap roots) obtained by drying, crushing or pulverizing the crude plant bodies.

The plants containing the resin glycosides include, for example, the plants of the convolvulus family such as *Pharbitis nil* Choisy, *Pharbitis hederacea* Choisy, *Quamoclit pennata* Bojer, *Ipomoea batatas* Lam, *Ipomea orizabensis* Ledanois, *Ipomea purga* and *Ipomea muricata* (L) Jacq. In particular, *Pharbitis nil* Choisy, *Pharbitis hederacea* Choisy, *Ipomea orizabensis* Ledanois and *Ipomea purga* are preferable, and *Pharbitis nil* Choisy and *Pharbitis hederacea* Choisy are more preferable.

When the purified resin glycosides are used in the present invention, they can be produced, for example, by the following methods.

With respect to the plants described above, the whole plant or parts thereof (such as cortices, flowers, seeds, leaves, roots and stems) containing the resin glycosides, which are in the raw or preferably fabricated, are extracted with about 5-fold to 10-fold amounts of sole or mixed solvents of alcohols such as absolute methanol, absolute ethanol, hydrous methanol and hydrous ethanol, ketones such as acetone and methyl ethyl ketone, chloroform and the like, at room temperature or elevated temperatures under reflux for 2 hours to 2 weeks. Extracted solutions are concentrated, and then subjected to column chromatography using polystyrene-series resins or dextran-series resins such as Diaion HP-20, Diaion XAD-2, MCI-Gel CHP-20 and Sephadex LH-20 to concentrate fractions eluted with alcohols, acetone, hydrous alcohols or hydrous acetone, whereby the purified resin glycosides can be obtained. After concentration of the extracted solutions, ethers such as diethyl ether are laid on the concentrates to allow resin glycosides to precipitate. Then, the purified resin glycosides can be obtained by filtration.

Magnolol and its derivatives will hereinafter be described. Magnolol is a compound represented by the following formula (IV):

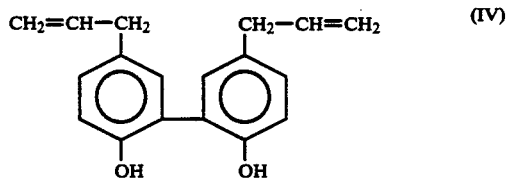
(IV)

As magnolol, there may be used purified magnolol, crude plant bodies containing magnolol such as the whole plant or parts (such as cortices, flowers, seeds, leaves, roots and stems) of plants containing magnolol, or preferably fabricated products (such as magnolia bark, Chinese magnolia bark, Japanese magnolia bark and Japanese magnolia nuts) obtained by drying, crushing or pulverizing the crude plant bodies.

The plants containing magnolol include the plants of the magnolia family such as *Magnolia obovata* Thunb and *Magnolia virginiana*. Examples of the magnolol derivatives of natural origin exhibiting strong antiprotozoal activity include honokiol [formula (V)], obovatol [formula (VI)]and tetrahydromagnolol [formula (VII)].

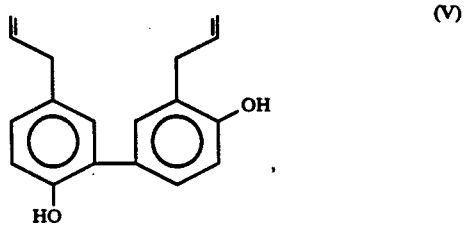
(V)

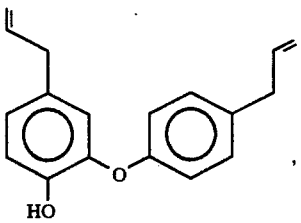
(VI)

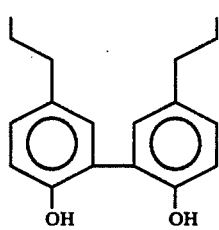
(VII)

As honokiol, obovatol and tetrahydromagnolol, there may be used purified ones, the wholes or parts (such as cortices, flowers, seeds, leaves, roots and stems) of crude plants containing one or more of these three components, or preferably fabricated products (such as magnolia bark, Japanese magnolia bark and Chinese magnolia bark) obtained by drying, crushing or pulverizing the crude plant bodies. The plants containing these components include the plants of the magnolia family such as *Magnolia obovata* Thunb and *Magnolia virginiana*.

Further, the magnolol derivatives may be synthetic compounds which include compounds represented by formula VIII:

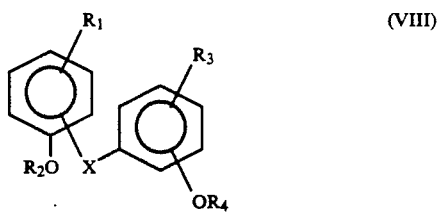
(VIII)

in which each of $R_1$ and $R_3$ represents hydrogen, halogen, alkyl of 1 to 6 carbon atoms which may have an oxygen functional group, or allyl, each of $R_2$ and $R_4$ represents hydrogen, alkyl of 1 to 4 carbon atoms, acyl or allyl, and X represents oxygen, sulfur or a linkage bond.

When purified magnolol is used in the present invention, it can be produced, for example, by the following methods.

With respect to the plants described above, the wholes or parts thereof (such as cortices, flowers, seeds, leaves, roots and stems) containing magnolol, which are in the raw or preferably fabricated, are crushed, followed by extraction, for example, with the sole solvents or hydrous solvents of acetone, alcoholic solvents such as methanol, and the like. However, the solvents are not limited thereto. The extraction is conducted using about 5-fold to 10-fold amounts of these solvents at room temperature or elevated temperatures under reflux for 2 hours to 2 weeks. Extracted solutions are concentrated, and then subjected to column chromatography using silica gel carriers, polystyrene-series resins or dextran-series resins such as Silica Gel 60, Diaion HP-20, MCI-Gel CHP-20 and Sephadex LH-20 to concentrate fractions eluted with petroleum ether, ethyl acetate, hydrous alcohols or hydrous acetone, whereby purified magnolol can be obtained.

Similarly, honokiol, obovatol and tetrahydromagnolol can be obtained using various carriers.

There have been no reports in the literature that magnolol and its derivatives exhibit antiprotozoal activity. It is also possible to use independently magnolol, its derivatives and the plant bodies containing them as preventive therapeutic agents for protozoiasis as with the condensed tannins, the resin glycosides and the plant bodies containing them.

When magnolol and its derivatives are used independently as prophylactic and therapeutic agents for protozoal disease, their dosage level will vary with circumstances such as the administrating method, the purpose of administration, the object to which the agents are administered, the type of disease to be treated, the protozoan species and the symptom of the disease. However, when plants containing magnolol and its derivatives or their fabricated products are incorporated in feed, they are usually preferably added in an amount of about 0.1 to 20% by weight based on the feed, and more preferably in an amount of about 2 to 10% by weight. In the case of magnolol, it is preferably added in an amount of about 250 to 2,000 ppm based on the feed, and more preferably in an amount of about 500 to 1,000 ppm. The addition amount of the magnolol derivatives such as honokiol, obovatol and tetrahydromagnolol to the feed is the same as that of magnolol. As described above, magnolol, its derivatives or plant bodies containing them can be used independently as prophylactic and therapeutic agents for protozoal disease. However, the combined use of them with the ionophore antibiotics cause the synergistic effect and the dosage level can also be reduced. It is therefore preferred to use them in combination with the ionophore antibiotics.

As the condensed tannins, the resin glycosides and magnolol described above, their derivatives may be used, as long as they exhibit antiprotozoal activity.

Examples of the plants containing the plant components having antiprotozoal activity in the present invention include plants whose antiprotozoal function has been known such as *Polyala tenuifolia, Bupleurinum falcatum, Fagara ailanthoides, Uncaria kawakamii, Lycoris radiate, Anemarrhena asphodeloides, Verbena officinalis, Carpesium abratanoides, Artemisia annua* and *Dichloa febrifuga*, and plants whose antiprotozoal function has been discovered by the present inventors such as *Cassia obtusifolia, Cassia acutifolia, Glycirrhzia echinata, Paeoniaceae lactiflora, Iodon japonicus* and *Lythospermum erythrorhizon*, other than the above-mentioned plants containing the condensed tannins, resin glycosides, magnolol or its derivatives.

As for the plants described above, there may be used the whole plant or parts thereof, the parts exhibiting antiprotozoal activity, preferably fabricated products obtained by drying, crushing or pulverizing them, fractions thereof or plant components having antiprotozoal activity and obtained by isolation and purification.

In the present invention, the plant components having antiprotozoal activity or the plant bodies containing them are used in combination with the ionophore antibiotics. Two or more kinds of the plant components having antiprotozoal activity or the plant bodies containing them may be used in combination. Further, plant bodies containing two or more kinds of the plant components having antiprotozoal activity, such as the whole of the plants containing two or more kinds of the plant components, or fractions or parts containing one or more kinds of the plant components, may be used as they are. Furthermore, the fabricated product obtained by drying, crushing or pulverizing them may also be used.

The ionophore antibiotics used in combination with the above-mentioned plant components having antiprotozoal activity or the plant bodies containing them include, for example, monensin, naracin, salinomycin, lasalocid, carriomycin, maduramicin and others, pharmacologically acceptable salts thereof and ester derivatives thereof.

When the plant components having antiprotozoal activity or the plant bodies (the whole plant or parts of the plants, the fractions and the fabricated products thereof) containing them are used in combination with the ionophore antibiotics, their dosage level will vary with circumstances such as the administrating method, the purpose of administration, the object to which the agents are administered, the type of disease to be treated, the protozoan species and the symptom of the disease. However, when the plant components or the plant bodies are incorporated in feed, they are usually preferably added in an amount of about 0.01 to 5.0% by weight based on the feed, and more preferably in an amount of about 0.01 to 2.0% by weight. When the plant bodies containing the condensed tannins are incorporated in the feed together with the ionophore antibiotics, they are usually added in an amount of about 0.02 to 4.0% by weight based on the feed, preferably in an amount of about 0.04 to 2.0% by weight, and more preferably in an amount of about 0.05 to 1.5% by weight. The plant bodies containing the resin glycosides are usually added in an amount of about 0.05 to 5.0% by weight based on the feed, and preferably in an amount of about 0.1 to 2.0% by weight. The plant bodies containing magnolol or its derivatives are usually added in an amount of about 0.01 to 5.0% by weight, and preferably in an amount of about 0.01 to 2.0% by weight. When the purified plant components having antiprotozoal activity are incorporated in the feed together with the ionophore antibiotics, the plant components are usually added in an amount of about 0.01 to 1.5% by weight based on the feed, and preferably in an amount of about 0.01 to 1.0% by weight. The purified condensed tannins are usually added in an amount of about 0.01 to 1.5% by weight based on the feed, and preferably in an amount of about 0.02 to 1.0% by weight. The purified resin glycosides are usually added in an amount of about 0.01 to 0.125% by weight based on the feed, and preferably in an amount of about 0.01 to 0.1% by weight. Purified magnolol is usually added in an amount of about 0.01 to 0.15% by weight based on the feed, and preferably in an amount of about 0.01 to 0.1% by weight.

On the other hand, the ionophore antibiotics which are incorporated in the feed together with the plant components having antiprotozoal activity, their derivatives or the plant bodies containing them are usually added to give concentrations one-half the recommended concentrations of the ionophore antibiotics to be incorporated in the feed to the recommended ones.

The plant components having antiprotozoal activity and the plant bodies containing them in the present invention are of natural origin and low in toxicity, so that they can be safely used in combination with the ionophore antibiotics as prophylactic and therapeutic agents for protozoal disease. For example, the purified condensed tannins, the whole plant or parts of the plants containing the condensed tannins, or their fabricated products are very low in toxicity. The 50% lethal dose (observed for 8 days after administration) on oral administration to nine-day-old White Leghorn male chicks is at least 20 g/kg/day for the purified condensed tannins, and at least 100 g/kg/day for the whole plant or parts of the plants containing the condensed tannins or their fabricated products (such as *Parabenzoin trilobum* N., bark of *Neolitsea aciculata* B., myristica, catechu and *Polygonum multiflorum*). Further, the purified resin glycosides, the wholes or parts of the plants containing the resin glycosides or their fabricated products are also very low in toxicity. For example, The 50% lethal dose (observed for 8 days after administration) on oral administration to nine-day-old White Leghorn male chicks is at least 1.0 g/kg/day for the purified resin glycosides, and at least 50 g/kg/day for the whole plant or parts of the plants containing the resin glycosides or their fabricated products (such as seeds of Pharbitis nil Choisy, seeds of Pharbitis hederacea Choisy and pharbitis seeds). Furthermore, purified magnolol or its derivatives, the whole plant or parts of the plants containing magnolol or its derivatives, or their fabricated products (such as magnolia bark, Japanese magnolia bark, Chinese magnolia bark) are also very low in toxicity. For example, with respect to the acute toxicity caused by oral administration of purified magnolol to mice, the $LD_{50}$ is 2200 mg/kg, so that it can be safely administered to live-stock animals such as chickens, quails, turkeys, cattle, swine and sheep.

On the other hand, the ionophore antibiotics are different from one another in toxicity. In general, however, the toxicity to the animals to which the antibiotics are administered is not developed unless the antibiotics are added at concentrations 1.5 to 2 times the recommended concentrations of antibiotics to be incorporated in feed for the prophylaxis and treatment of coccidiosis (the permitted concentrations somewhat differ with countries). From this fact, the safety of the ionophore antibiotics on use has already been established, and the ionophore antibiotics actually come into wide use based thereon.

The ionophore antibiotics and the plant components having antiprotozoal activity or the plant bodies containing them are added to feed in combination so as to give the above-mentioned addition amounts. It is usually desirable to use the plant components having antiprotozoal activity or the plant bodies containing them in an amount of about 0.01 to 1.5% by weight, and preferably in an amount of about 0.02 to 1.0% by weight, based on the feed, when the ionophore antibiotics are used at concentrations ½ to 1 time the recommended concentrations of ionophore antibiotics to be added to feed (for example, in the case of monensin, it is recommended to add 80 to 120 ppm to feed for coccidiosis).

The prophylactic and therapeutic agent for protozoal disease of the present invention can be prepared by mixing these materials to formulate a preparation according to a known pharmaceutical method, using a pharmaceutically acceptable additive(s) such as a diluent and an excipient, if necessary, and formed to a preparation when used, followed by incorporation in feed or drinking water for administration. Further, the materials independently formulated as described above can be separately administered by the same route or different routes, at the same time or at intervals.

The prophylactic and therapeutic agent for protozoal disease of the present invention is prepared, for example, by diluting the ionophore antibiotic and the plant component having antiprotozoal activity or the plant body containing it, independently or in a mixed state, with a solid or liquid carrier, by concentrating them, or by stabilizing them by coating and the like to formulate powders, dusts, granules, tablets, solutions, emulsions, pastes, capsules, premixed, injections and the like. The prophylactic and therapeutic agent of the present invention is also prepared by dispersing directly the ionophore antibiotic and the plant component having antiprotozoal activity or the plant body containing it in feed, drink and the like, or by incorporating therein the ionophore antibiotic and the plant component having antiprotozoal activity or the plant body containing it which have been dispersed in a carrier. The carrier may be any one, as long as it is physiologically harmless per se. The carriers which function as feed or a component of feed are preferable. The solid carriers include, for example, lactose, sucrose, starch, wheat meal, corn meal, wheat bran, soybean cake, extracted rice bran, rape seed cake, soybean crude meal, cellulose yeast, fish meal, peanut meal, shell powder and calcium carbonate. Examples of the liquid carriers include water, physiological saline and physiologically acceptable organic solvents. In addition, other suitable adjuvants such as emulsifiers, dispersants, suspension aids, wetting agents, thickening agents, gel forming agents and solubilizers may be added in suitable amounts. It is also possible to use the plant component having antiprotozoal activity or the plant body containing it, as a carrier for the ionophore antibiotic to formulate a premix preparation. There may be further incorporated preservatives, fungicides, colorants, aromatics, antibacterial agents, antibiotics, enzyme preparations, lactobacillus preparations, antifebriles, analgesics, antiphlogistics and so on, and other prophylactic and therapeutic agents for protozoal disease may also be compounded in combination. Furthermore, various vitamins, minerals and amino acids may be incorporated.

The prophylactic and therapeutic agents for protozoal disease of the present invention are administered to live-stock animals, for the purpose of prophylaxis or/and treating protozoal disease. In the live-stock industry, domestic animals are usually bred in groups. It is therefore also included in the scope of this invention of course to administer the prophylactic and therapeutic agents for protozoal disease of the present invention to infected individuals isolated from the group or to the whole of the group through feed, drinking water and the like, when it has been confirmed that some animals in the group are attacked with protozoal disease.

Examples of the diseases for which the prophylactic and therapeutic agents for protozoal disease of the present invention are administered include avian coccidiosis, avian leucocytozoon disease, coccidiosis in swine or cattle, toxoplasmosis, malaria, piroplasmosis, human malaria, tropical fevers, etc. In particular, the prophylactic and therapeutic agents of this invention are suitable for coccidiosis in chickens, turkeys and quails, and coccidiosis in cattle.

The amount used of the ionophore antibiotics whose safety range is pointed out to be relatively narrow can be reduced by using the antiprotozoal drugs of the present invention, and further, the possibility of gaining the ionophore resistance can be reduced. The prophylactic and therapeutic agents of the present invention are therefore advantageous in respect to the safety in the use of the drugs to live-stock animals and the avoidance of the resistance. Furthermore, the prophylactic and therapeutic agents of this invention exhibit sufficient antiprotozoal activity in low dosage level, and also exhibit antiprotozoal activity to protozoa having reduced sensitivity to the ionophore antibioties. Thus, the preventive therapeutic agents of this invention are safety and economical, and give the excellent effect to protozoal disease, so that they are particularly useful for the live-stock industry.

The present invention will hereinafter be described in detail with the following Examples. It is understood of course that these Examples are not intended to limit the scope of the invention.

EXAMPLE 1

The effect of the drugs to coccidiosis was examined using chicks. Namely, nine-day-old White Leghorn male chicks were divided into groups each of which consists of 3 chicks, and $5 \times 10^4$ sporulated oocysts per chick of laboratory standard strain *Eimeria tenella* were orally inoculated into the chicks in all groups except for the control group in which the chicks were not infected and not dosed with the drugs, at 24 hours after the start of dosing. Prescribed amounts of respective plant components dried and crushed and monensin sodium or salinomycin sodium were added to the basal feed (SDL No. 1: Nippon Haigo Shiryo), and continuously administered by the free ingesting method for 9 days from 24 hours before infection to 8 days after infection. The weight of each chick was measured, and the bloody dropping were observed. Further, the chicks were autopsied at day-8 after infection to examine the caecel lesion. Thus, the anticoccidial effect of the administered test drugs was determined. The results are shown in Table 1.

As apparent from the results shown in Table 1, it is proved that the groups of the present invention are increased in weight gain ratio in comparison to the group infected and unmedicated, and exhibit excellent synergistic anticoccidial function with a combined total dose of not more than 1, when the dose with which each drug can independently depress coccidiosis is taken as 1 and the combined dose thereof is taken as 2.

TABLE 1

Combined Effect of Monensin and Various Crude Drugs to Laboratory Standard Strain *Eimeria tenella*

| Test Group | | ppm | % | No. of Bloody[2) Droppings | Mortality |
|---|---|---|---|---|---|
| Uninfected, unmedicated control (UUC) | | | | 0 | 0/9 |
| Infected, unmedicated control (IUC) | | | | 13.3 | 3/9 |
| Monensin | — | 40 | | 13.3 | 1/3 |
| Monensin | — | 60 | | 7.3 | 0/3 |
| Monensin | — | 80 | | 1.0 | 0/6 |
| Monensin | — | 120 | | 0 | 0/6 |
| — | Catechu | | 2.5 | 11.7 | 1/3 |
| — | Catechu | | 5.0 | 0 | 0/3 |
| Monensin + | Catechu | 80 + | 2.5 | 0 | 0/3 |
| Monensin + | Catechu | 100 + | 0.1 | 0 | 0/3 |
| — | Pharbitis seeds | | 0.5 | 11.7 | 0/3 |
| — | Pharbitis seeds | | 1.0 | 0.3 | 0/3 |

TABLE 1-continued

Combined Effect of Monensin and Various Crude Drugs to Laboratory Standard Strain *Eimeria tenella*

| Test Group | | ppm | % | No. of Bloody[2] Droppings | Mortality |
|---|---|---|---|---|---|
| — | Pharbitis seeds | | 2.0 | 0 | 0/3 |
| — | Pharbitis seeds | | 5.0 | 0 | 0/3 |
| Monensin + | Pharbitis seeds | 40 + | 0.5 | 8.3 | 0/3 |
| Monensin + | Pharbitis seeds | 60 + | 0.5 | 1.0 | 0/3 |
| Monensin + | Pharbitis seeds | 40 + | 1.0 | 1.3 | 0/3 |
| Monensin + | Pharbitis seeds | 60 + | 1.0 | 0 | 0/3 |

| Test Group | | Caecal[3] Lesion | Weight Gain[1] Ratio (%) | OPG[4] (log) |
|---|---|---|---|---|
| UUC | | 0 | 100.0 | ND |
| IUC | | 4.0 | 53.6 | 4.8 |
| Monensin | — | 4.0 | 36.7 | 4.5 |
| Monensin | — | 4.0 | 92.9 | 4.6 |
| Monensin | — | 2.2 | 103.2 | 4.3 |
| Monensin | — | 0 | 103.2 | 3.4 |
| — | Catechu | 4.0 | 90.0 | 5.3 |
| — | Catechu | 0 | 78.9 | ND |
| Monensin + | Catechu | 0 | 99.9 | ND |
| Monensin + | Catechu | 0.3 | 95.8 | 2.0 |
| — | Pharbitis seeds | 4.0 | 79.0 | 5.2 |
| — | Pharbitis seeds | 2.7 | 87.4 | 5.4 |
| — | Pharbitis seeds | 2.3 | 102.6 | 4.4 |
| — | Pharbitis seeds | 2.7 | 80.2 | 2.6 |
| Monesin + | Pharbitis seeds | 4.0 | 75.4 | 4.9 |
| Monesin + | Pharbitis seeds | 3.0 | 97.7 | 4.9 |
| Monesin + | Pharbitis seeds | 2.7 | 93.8 | 4.6 |
| Monesin + | Pharbitis seeds | 2.3 | 106.6 | 4.5 |

| Test Group | | ppm | % | No. of Bloody[2] Droppings | Mortality |
|---|---|---|---|---|---|
| Monensin + | Pharbitis seeds | 40 + | 2.0 | 0 | 0/3 |
| Monensin + | Pharbitis seeds | 60 + | 2.0 | 0 | 0/3 |
| Monensin + | Pharbitis seeds | 100 + | 0.1 | 0 | 0/3 |
| — | Parabenzoin trilobum N. | | 1.0 | 11.7 | 0/3 |
| — | Parabenzoin trilobum N. | | 2.5 | 13.3 | 1/3 |
| — | Parabenzoin trilobum N. | | 5.0 | 13.3 | 2/3 |
| — | Parabenzoin trilobum N. | | 10.0 | 0 | 0/3 |
| Monesin + | Parabenzoin trilobum N. | 40 + | 0.5 | 4.3 | 0/3 |
| Monesin + | Parabenzoin trilobum N. | 60 + | 0.5 | 0.3 | 0/3 |
| Monesin + | Parabenzoin trilobum N. | 80 + | 0.5 | 0 | 0/3 |
| Monesin + | Parabenzoin trilobum N. | 40 + | 1.0 | 0.3 | 0/3 |
| Monesin + | Parabenzoin trilobum N. | 60 + | 1.0 | 0 | 0/3 |
| Monesin + | Parabenzoin trilobum N. | 80 + | 1.0 | 0 | 0/3 |
| Monesin + | Parabenzoin trilobum N. | 40 + | 2.5 | 0 | 0/3 |
| Monesin + | Parabenzoin trilobum N. | 60 + | 2.5 | 0 | 0/3 |
| Monesin + | Parabenzoin trilobum N. | 100 + | 0.25 | 0 | 0/3 |

| Test Group | | Lesion | Ratio (%) | (log) |
|---|---|---|---|---|
| Monensin + | Pharbitis seeds | 2.7 | 90.5 | 3.4 |
| Monensin + | Pharbitis seeds | 1.7 | 107.3 | 3.2 |
| Monensin + | Pharbitis seeds | 1.0 | 92.9 | 2.7 |
| — | Parabenzoin trilobum N. | 4.0 | 28.8 | 5.0 |
| — | Parabenzoin trilobum N. | 4.0 | 14.1 | 4.7 |
| — | Parabenzoin trilobum N. | 4.0 | 42.1 | 4.1 |
| — | Parabenzoin trilobum N. | 2.0 | 88.6 | 4.9 |
| Monensin + | Parabenzoin trilobum N. | 2.3 | 71.0 | 4.7 |
| Monensin + | Parabenzoin trilobum N. | 2.3 | 93.6 | 3.7 |
| Monensin + | Parabenzoin trilobum N. | 0.3 | 97.7 | 2.0 |
| Monensin + | Parabenzoin trilobum N. | 1.0 | 103.4 | 4.3 |
| Monensin + | Parabenzoin trilobum N. | 0.7 | 101.8 | 2.7 |
| Monensin + | Parabenzoin trilobum N. | 0.3 | 98.8 | ND |
| Monensin + | Parabenzoin trilobum N. | 1.0 | 106.6 | 2.7 |
| Monensin + | Parabenzoin trilobum N. | 0.3 | 104.9 | ND |
| Monensin + | Parabenzoin trilobum N. | 0 | 92.9 | ND |

| Test Group | | ppm | % | No. of Bloody[2] Droppings | Mortality |
|---|---|---|---|---|---|
| — | Japanese magnolia bark | | 2.5 | 6.7 | 0/3 |
| — | Japanese magnolia bark | | 5.0 | 3.3 | 0/3 |
| Monensin + | Japanese magnolia bark | 40 + | 2.5 | 0 | 0/3 |
| Monensin + | Japanese magnolia bark | 40 + | 5.0 | 0 | 0/3 |
| Monensin + | Japanese magnolia bark | 80 + | 2.5 | 0 | 0/3 |
| Monensin + | Japanese magnolia bark | 80 + | 5.0 | 0 | 0/3 |
| — | Magnolol | | 125 (ppm) | 13.3 | 0/3 |
| — | Magnolol | | 250 (ppm) | 3.7 | 0/3 |
| — | Magnolol | | 500 (ppm) | 1.3 | 0/3 |
| Monensin + | Magnolol | 40 + | 125 (ppm) | 6.7 | 0/3 |
| Monensin + | Magnolol | 60 + | 125 (ppm) | 1.0 | 0/3 |
| Monensin + | Magnolol | 40 + | 250 (ppm) | 1.0 | 0/3 |
| Monensin + | Magnolol | 60 + | 250 (ppm) | 2.0 | 0/3 |
| — | Honokiol | | 125 (ppm) | 13.3 | 1/3 |
| — | Honokiol | | 500 (ppm) | 1.0 | 0/3 |
| Monensin + | Honokiol | 40 + | 125 (ppm) | 6.7 | 0/3 |
| Monensin + | Honokiol | 60 + | 125 (ppm) | 5.0 | 0/3 |

Caecal[3]  Weight Gain[1]  OPG[4]

TABLE 1-continued

Combined Effect of Monensin and Various Crude Drugs to Laboratory Standard Strain *Eimeria tenella*

| Test Group | | Lesion | Ratio (%) | (log) |
|---|---|---|---|---|
| — | Japanese magnolia bark | 3.7 | 73.2 | 5.0 |
| — | Japanese magnolia bark | 3.3 | 89.5 | 5.4 |
| Monensin + | Japanese magnolia bark | 2.3 | 111.3 | 4.7 |
| Monensin + | Japanese magnolia bark | 2.0 | 106.8 | 5.2 |
| Monensin + | Japanese magnolia bark | 0 | 101.1 | 4.3 |
| Monensin + | Japanese magnolia bark | 0.3 | 103.9 | ND |
| — | Magnolol | 4.0 | 62.5 | 5.3 |
| — | Magnolol | 4.0 | 89.3 | 5.8 |
| — | Magnolol | 3.3 | 94.5 | 3.2 |
| Monensin + | Magnolol | 4.0 | 73.0 | 5.1 |
| Monensin + | Magnolol | 3.0 | 92.2 | 4.5 |
| Monensin + | Magnolol | 4.0 | 94.6 | 4.8 |
| Monensin + | Magnolol | 2.3 | 104.2 | 4.7 |
| — | Honokiol | 4.0 | 41.6 | 5.1 |
| — | Honokiol | 3.3 | 99.4 | 4.9 |
| Monensin + | Honokiol | 3.7 | 75.4 | 5.0 |
| Monensin + | Honokiol | 3.7 | 95.3 | 5.2 |

Note [1] Weight gain ratio = (Average weight gain for each test group/Average weight gain for uninfected, unmedicated control group) × 100 (%)
Note [2] The bloody feces index is indicated by the number of bloody droppings observed on litter as the amount of bloody feces excreted from the ceca of chicks.
Note [3] The caecal lesion is indicated by an average score when scored taking 0 for a normal condition, 1 for a slightly damaged condition, 2 for a condition damaged to a middle degree, 3 for a severely damaged condition and 4 for a very severely damaged condition [Johnson and Reid, Exp. Parasitol. 28, 30–36 (1970)].
Note [4] The OPG shows the number of oocysts excreted in 1 g of feces (at day-7 after infection).
Note [5] The ND means "not detected".

EXAMPLE 2

The effect to field isolate *Eimeria tenella* (AMD) exhibiting resistance against the ionophore antibiotics was determined similarly to Example 1. The oocysts were inoculated at a rate of 30,000 per chick. The results obtained when monensin or salinomycin and the crude drug of *Parabenzoin trilobum* N. containing the condensed tannin as a main component were administered in combination are shown in Table 2.

TABLE 2

Combined Effect of Monensin or Salinomycin and *Parabenzoin trilobum* N. to Field Isolate *Eimeria tenella* (AMD)

| Test Group | | ppm | % | No. of Bloody Droppings | Mortality |
|---|---|---|---|---|---|
| Uninfected, unmedicated control (UUC) | | | | 0 | 0/10 |
| Infected, unmedicated control (IUC) | | | | 14.0 | 1/5 |
| Monensin | — | 80 | | 10.0 | 0/5 |
| Monensin | — | 100 | | 8.0 | 0/5 |
| Monensin | — | 160 | | 0 | 0/5 |
| Salinomycin | — | 50 | | 9.0 | 0/5 |
| — | Parabenzoin trilobum N. | | 1.0 | 14.0 | 2/5 |
| — | Parabenzoin trilobum N. | | 10.0 | 0 | 0/5 |
| Monensin + | Parabenzoin trilobum N. | 60 + | 0.5 | 1.4 | 0/5 |
| Monensin + | Parabenzoin trilobum N. | 80 + | 0.5 | 0.2 | 0/5 |
| Monensin + | Parabenzoin trilobum N. | 60 + | 1.0 | 1.2 | 0/5 |
| Monensin + | Parabenzoin trilobum N. | 80 + | 1.0 | 0.6 | 0/5 |
| Monensin + | Parabenzoin trilobum N. | 100 + | 0.1 | 2.8 | 0/5 |
| Salinomycin + | Parabenzoin trilobum N. | 50 + | 0.5 | 5.0 | 0/5 |

| Test Group | | Caecal Lesion | Weight Gain Ratio (%) | OPG (log) |
|---|---|---|---|---|
| UUC | | 0 | 100.0 | ND |
| IUC | | 4.0 | 38.2 | 6.3 |
| Monensin | — | 4.0 | 54.8 | 6.2 |
| Monensin | — | 4.0 | 72.6 | 6.1 |
| Monensin | — | 0.4 | 81.5 | ND |
| Salinomycin | — | 3.2 | 80.3 | 5.8 |
| — | Parabenzoin trilobum N. | 4.0 | 39.1 | 6.2 |
| — | Parabenzoin trilobum N. | 1.6 | 88.7 | 4.9 |
| Monensin + | Parabenzoin trilobum N. | 0.8 | 85.4 | 5.1 |
| Monensin + | Parabenzoin trilobum N. | 2.2 | 99.4 | 6.1 |
| Monensin + | Parabenzoin trilobum N. | 1.4 | 95.5 | 5.6 |
| Monensin + | Parabenzoin trilobum N. | 1.6 | 95.0 | 5.6 |
| Monensin + | Parabenzoin trilobum N. | 1.0 | 87.9 | 5.9 |
| Salinomycin + | Parabenzoin trilobum N. | 2.2 | 82.5 | 5.9 |

As shown in Table 2, the groups in which the ionophore antibiotics and the crude drug of *Parabenzoin trilobum* N. were used in combination is apparently more excellent in synergistic depression effect than the groups in which each was independently used. In particular, no distinct depression effect can be observed for the ionophore antibiotics at concentrations in common use. In contrast, the examples in which the drug of *Parabenzoin trilobum* N. was administered in combination with the ionophore antibiotics at the same concentrations as described above apparently exhibit excellent depression effect. Monensin does not show sufficient antiprotozoal activity until it is administered at a concentration of 160 ppm much higher than the concentrations in common use.

EXAMPLE 3

The combined administration effect of monensin and the crude drug of pharbitis seeds containing the resin glycoside as a main component was examined, by an infection experiment method in accordance with the method in Example 2. The results are shown in Table 3.

TABLE 3

Combined Effect of Monensin and Pharbitis Seeds to Field Isolate *Eimeria tenella* (AMD)

| Test Group | | ppm | % | No. of Bloody Droppings | Mortality |
|---|---|---|---|---|---|
| Uninfected, unmedicated control (UUC) | | | | 0 | 0/10 |
| Infected, unmedicated conrol (IUC) | | | | 14.0 | 1/5 |
| Monensin | — | 80 | | 10.0 | 0/5 |
| Monensin | — | 100 | | 8.0 | 0/5 |
| Monensin | — | 160 | | 0 | 0/5 |

TABLE 3-continued

Combined Effect of Monensin and Pharbitis
Seeds to Field Isolate *Eimeria tenella* (AMD)

| | | | | |
|---|---|---|---|---|
| — | Pharbitis seeds | 1.0 | 9.0 | 1/5 |
| — | Pharbitis seeds | 5.0 | 0 | 0/5 |
| Monensin + | Pharbitis seeds | 60 + 0.5 | 4.4 | 0/5 |
| Monensin + | Pharbitis seeds | 80 + 0.5 | 3.8 | 0/5 |
| Monensin + | Pharbitis seeds | 60 + 1.0 | 3.6 | 0/5 |
| Monensin + | Pharbitis seeds | 80 + 1.0 | 1.6 | 0/5 |
| Monensin + | Pharbitis seeds | 100 + 0.1 | 1.2 | 0/5 |

| Test Group | | Caecal Lesion | Weight Gain Ratio (%) | OPG (log) |
|---|---|---|---|---|
| UUC | | 0 | 100.0 | ND |
| IUC | | 4.0 | 38.2 | 6.3 |
| Monensin | — | 4.0 | 54.8 | 6.2 |
| Monensin | — | 4.0 | 72.6 | 6.1 |
| Monensin | — | 0.4 | 81.5 | ND |
| — | Pharbitis seeds | 4.0 | 76.4 | 6.3 |
| — | Pharbitis seeds | 2.6 | 80.1 | 2.7 |
| Monensin + | Pharbitis seeds | 3.6 | 81.5 | 5.8 |
| Monensin + | Pharbitis seeds | 2.0 | 91.7 | 5.5 |
| Monensin + | Pharbitis seeds | 2.2 | 90.4 | 5.5 |
| Monensin + | Pharbitis seeds | 1.6 | 85.4 | 5.0 |
| Monensin + | Pharbitis seeds | 1.8 | 96.8 | 5.9 |

As shown in Table 3, the groups in which the ionophore antibiotic and the crude drug of pharbitis seeds were used in combination is apparently more excellent in synergistic depression effect than the groups in which each was independently used. Monensin does not show sufficient antiprotozoal activity until it is administered at a concentration of 160 ppm much higher than the concentrations in common use.

EXAMPLE 4

The combined administration effect of monensin and Japanese magnolia bark containing magnolol as a main component was examined, by an infection experiment method in accordance with the method in Example 2. The results are shown in Table 4.

TABLE 4

Combined Effect of Monensin and Japanese Magnolia
Bark to Field Isolate *Eimeria tenella* (AMD)

| Test Group | | ppm | % | No. of Bloody Droppings | Mortality |
|---|---|---|---|---|---|
| Uninfected, unmedicated control (UUC) | | | | 0 | 0/10 |
| Infected, unmedicated conrol (IUC) | | | | 14.0 | 1/10 |
| Monensin | — | 80 | | 9.0 | 0/5 |
| Monensin | — | 160 | | 0 | 0/5 |
| Monensin | — | 240 | | 0 | 0/5 |
| — | Japanese magnolia bark | | 0.5 | 3.2 | 0/5 |
| — | Japanese magnolia bark | | 1.0 | 5.0 | 0/5 |
| — | Japanese magnolia bark | | 2.5 | 4.8 | 0/5 |

TABLE 4-continued

Combined Effect of Monensin and Japanese Magnolia
Bark to Field Isolate *Eimeria tenella* (AMD)

| | | | | |
|---|---|---|---|---|
| Monensin + | Japanese magnolia bark | 80 + 0.5 | 0.6 | 0/5 |
| Monensin + | Japanese magnolia bark | 40 + 1.0 | 1.0 | 0/5 |
| Monensin + | Japanese magnolia bark | 60 + 1.0 | 0 | 0/5 |
| Monensin + | Japanese magnolia bark | 80 + 1.0 | 0 | 0/5 |
| Monensin + | Japanese magnolia bark | 40 + 2.5 | 0.2 | 0/5 |
| Monensin + | Japanese magnolia bark | 60 + 2.5 | 0.4 | 0/5 |
| Monensin + | Japanese magnolia bark | 80 + 2.5 | 0 | 0/5 |

| Test Group | | Caecal Lesion | Weight Gain Ratio (%) | OPG (log) |
|---|---|---|---|---|
| UUC | | 0 | 100.0 | ND |
| IUC | | 4.0 | 55.5 | 6.4 |
| Monensin | — | 3.8 | 72.3 | 6.1 |
| Monensin | — | 1.2 | 86.5 | 4.7 |
| Monensin | — | 0 | 46.5 | ND |
| — | Japanese magnolia bark | 3.6 | 91.6 | 6.0 |
| — | Japanese magnolia bark | 3.2 | 94.2 | 6.0 |
| — | Japanese magnolia bark | 3.2 | 86.5 | 6.3 |
| Monensin + | Japanese magnolia bark | 2.2 | 94.2 | 5.6 |
| Monensin + | Japanese magnolia bark | 2.4 | 90.3 | 5.8 |
| Monensin + | Japanese magnolia bark | 1.6 | 100.6 | 5.0 |
| Monensin + | Japanese magnolia bark | 2.2 | 92.9 | 5.1 |
| Monensin + | Japanese magnolia bark | 2.6 | 100.6 | 5.6 |
| Monensin + | Japanese magnolia bark | 3.2 | 98.1 | 5.7 |
| Monensin + | Japanese magnolia bark | 2.2 | 95.5 | 5.0 |

EXAMPLE 5

The combined administration effect of the ionophore antibiotics and Rhizophoraceae bark was examined, by an infection experiment method in accordance with the method in Example 1. The results are shown in Table 5.

TABLE 5

Combined Effect of Ionophore Antibiotics and
Rhizophoraceae Bark to Laboratory Standard Strain
*Eimeria tenella* (AMD)

| Test Group | | ppm | % | No. of Bloody Droppings | Mortality |
|---|---|---|---|---|---|
| Uninfected, unmedicated control (UUC) | | | | 0 | 0/9 |
| Infected, unmedicated conrol (IUC) | | | | 13.3 | 2/9 |
| Monensin | — | 80 | | 5.0 | 0/9 |
| Salinomycin | — | 50 | | 7.0 | 1/9 |
| — | Rhizophoraceae bark | | 0.1 | 13.3 | 1/6 |
| — | Rhizophoraceae bark | | 0.5 | 12.0 | 1/6 |

TABLE 5-continued

Combined Effect of Ionophore Antibiotics and Rhizophoraceae Bark to Laboratory Standard Strain *Eimeria tenella* (AMD)

| | | | | | |
|---|---|---|---|---|---|
| — | Rhizophoraceae bark | | 10.0 | 0 | 0/3 |
| Monensin + | Rhizophoraceae bark | 80 + | 0.05 | 4.0 | 0/6 |
| Monensin + | Rhizophoraceae bark | 80 + | 0.1 | 1.7 | 0/6 |
| Monensin + | Rhizophoraceae bark | 80 + | 0.5 | 0 | 0/6 |
| Salinomycin + | Rhizophoraceae bark | 50 + | 0.1 | 5.0 | 0/9 |
| Salinomycin + | Rhizophoraceae bark | 50 + | 0.5 | 3.0 | 0/9 |

| Test Group | | Caecal Lesion | Weight Gain Ratio (%) |
|---|---|---|---|
| UUC | | 0 | 100 |
| IUC | | 4.0 | 40 |
| Monensin | — | 3.2 | 88 |
| Salinomycin | — | 3.6 | 62 |
| — | Rhizophoraceae bark | 4.0 | 40 |
| — | Rhizophoraceae bark | 4.0 | 40 |
| — | Rhizophoraceae bark | 0 | 89 |
| Monensin + | Rhizophoraceae bark | 2.3 | 97 |
| Monensin + | Rhizophoraceae bark | 1.8 | 95 |
| Monensin + | Rhizophoraceae bark | 2.7 | 95 |
| Salinomycin + | Rhizophoraceae bark | 3.5 | 76 |
| Salinomycin + | Rhizophoraceae bark | 2.9 | 82 |

EXAMPLE 6

Using the mixed strain (large size oocysts: 5%, middle size oocysts: 72%, small size oocysts: 23%) collected in the field and containing five or more kinds of coccidia, the combined administration effect of monensin and Rhizophoraceae bark against chicks infected with 10,000 oocysts per chick was examined, by an infection experiment method in accordance with the method in Example 1. The results are shown in Table 6. In Table 6, the general intestine lesion value was obtained by converting the sum of values judged by the five steps from 0 to +4 to a value per chick, for the lesion of upper, middle and lower parts of small intestine and caecum, according to the method described in Johnson and Reid, *Exp. Parasitol.* 28, 30–36 (1970). Other determinations were carried out in the same manner as with Example 1.

TABLE 6

Combined Effect of Monensin and Rhizophoraceae Bark to Chicks Infected with Field Chicken Coocidia of Mixed Species

| Test Group | | ppm | % | No. of Bloody Droppings | Mortality |
|---|---|---|---|---|---|
| Uninfected, unmedicated control (UUC) | | | | 0 | 0/6 |
| Infected, unmedicated control (IUC) | | | | 9.0 | 2/6 |
| Monensin | — | 80 | | 6.0 | 1/6 |
| Monensin + | Rhizophoraceae bark | 80 + | 0.1 | 3.7 | 0/6 |
| Monensin + | Rhizophoraceae bark | 80 + | 0.5 | 2.0 | 0/6 |

| | | Weight Gain | |

TABLE 6-continued

Combined Effect of Monensin and Rhizophoraceae Bark to Chicks Infected with Field Chicken Coocidia of Mixed Species

| Test Group | | Caecal Lesion | Ratio (%) |
|---|---|---|---|
| UUC | | 0 | 100 |
| IUC | | 9.0 | 71 |
| Monensin | — | 5.5 | 89 |
| Monensin + | Rhizophoraceae bark | 2.5 | 94 |
| Monensin + | Rhizophoraceae bark | 2.3 | 104 |

The following references, which are referred to for their disclosures at various points in this application, are incorporated herein by reference.

Avian Diseases 30, 690–694 (1986)

Collected Summaries of Lectures at 103rd Meeting of Japanese Veterinary Society VI-1, 150 (1987)

Drugs for Animals: Remaining of Feed Additives in Animal and Marine Products and Analytical Methods of the Same, Research Institute for Animal Science Biochemistry and Toxicology (1985)

Japanese Patent Unexamined Publication Nos. 63-196514/1988 and 63-196523/1988

Modern Japanese and Chinese Medicated Botany, published on Sep. 10, 1959

Iconographical Chinese Medicinal Dictionary Chinese Pharmaceutical Dictionary, published by Kodansha on May, 10, 1982

Collected Summaries of Lectures at 27th Natural Organic Compound Discussion Meeting 427–434 (1985)

Exp. Parasitol. 28, 30–36 (1970)

What is claimed is:

1. A method for the treatment of coccidiosis which comprises administering to a domestic animal requiring such treatment an anticoccidially effective amount of a combination of (A) a plant component having anticoccidiosis activity containing a member selected from the group consisting of (i) a condensed tannin represented by the formula

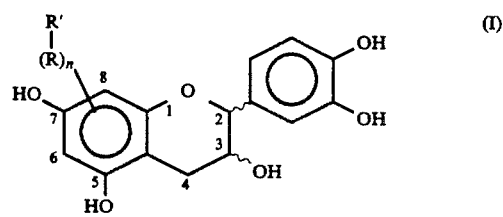
(I)

wherein

R is

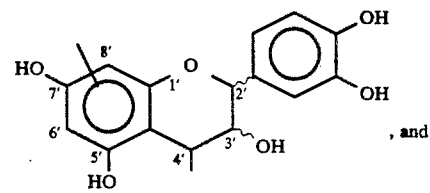
, and

R' is

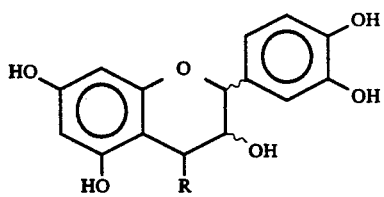

and in which n is an integer of 1 to 15, the 4' position of R is bound to the 6 position or the 8 position of formula (I), R' is bound to the 6' position or the 8' position of R, and when n is an integer of 2 to 15, the 4' position of R is bound to the 6' position or the 8' position of R (2) a resin glycoside represented by formula (II) or (III):

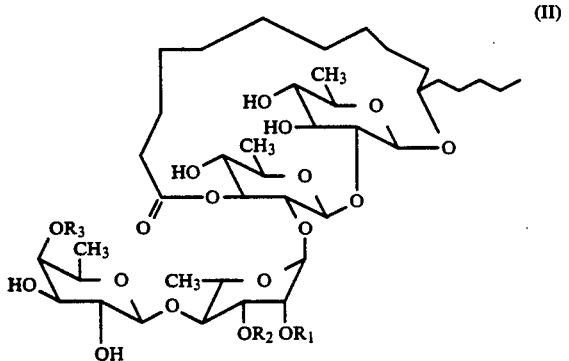

wherein $R_1$ and $R_2$ are independently hydrogen or α-methylbutyric acid or isobutyric acid,

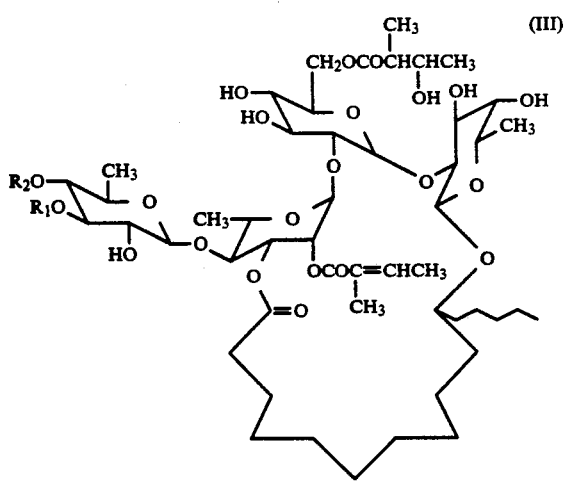

wherein $R_1$ is hydrogen or isobutyric acid and $R_2$ is hydrogen, α-methylbutyric acid, isobutyric acid or nilic acid, and (3) a magnolol derivative represented by the formula

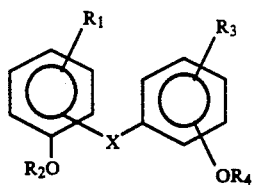

in which each of $R_1$ and $R_3$ represents hydrogen, halogen, alkyl of 1 to 6 carbon atoms which may have an oxygen functional group, or allyl, each of $R_2$ and $R_4$ represents hydrogen, alkyl of 1 to 4 carbon atoms, acyl or allyl, and X represents oxygen, sulfur or a linkage bond, and (B) an ionophore antibiotic having anticoccidiosis activity selected from the group consisting of monensin, naracin, salinomycin, lasalocid, carriomycin, maduramicin, a pharmacologically acceptable salt of such antibiotics and a pharmacologically acceptable ester of such antibiotics, the ratio of the plant component (A) to ionophore antibiotic (B) being such that in a feed composition containing the combination in which said ionophore antibiotics is employed in a concentration of from ¼ to 1 times the recommended concentration thereof, the plant component is present in an amount of from 0.01 to 1.5% by weight of said feed composition.

2. A method according to claim 1, wherein the plant component is Rhizophoraceae bark and the ionophore antibiotic is monensin.

3. A method according to claim 1, wherein both the plant component and the ionophore antibiotic is orally administered ad libitum in the form of an orally administerable feed.

4. A method according to claim 3, wherein the feed is produced by incorporating 0.01 to 1.5 % by weight of purified component (A) having anticoccidial activity in a feed containing an effective amount of the ionophore antibiotic.

5. A method according to claim 4, wherein the purified component (A) is incorporated in the feed in an amount of 0.01 to 1.0% by weight based on the feed.

6. A method according to claim 3, wherein the feed is produced by incorporating 0.01 to 5.0 % by weight of an unpurified component (A) having anticoccidial activity in a feed containing an effective amount of an ionophore antibiotic.

7. A method according to claim 6, wherein the unpurified component (A) is incorporated in the feed in an amount of 0.01 to 2.0% by weight based on the feed.

8. A method for the prophylaxis of coccidiosis which comprises administering to a domestic animal requiring such prophylaxis an anticoccidially effective amount of a combination of (A) a plant component having anticoccidiosis activity containing a member selected from the group consisting of (1) a condensed tannin represented by the formula

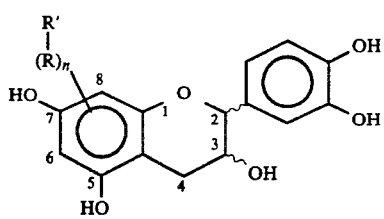
(I)

wherein
R is

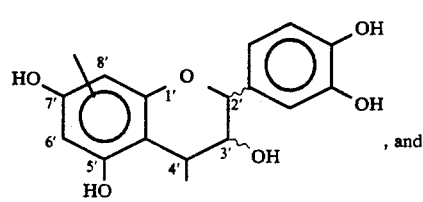
, and

R' is

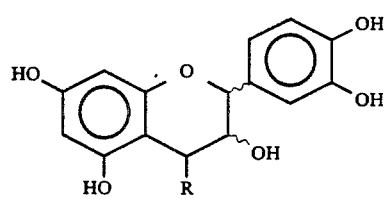

and in which n is an integer of 1 to 15, the 4''
position of R is bound to the 6 position or the 8
position of formula (I), R' is bound to the 6'
position or the 8' position of R, and when n is an
integer of 2 to 15, the 4' position of R is bound to
the 6' position or the 8' position of R (2) a resin glycoside represented by formula (II) or (III):

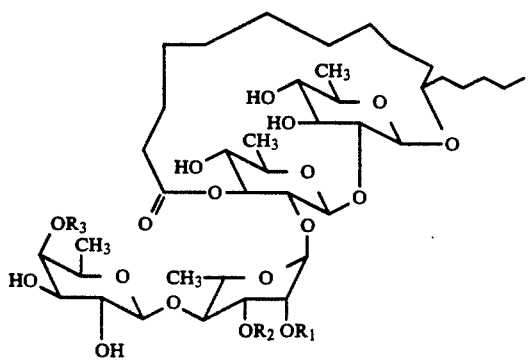
(II)

wherein $R_1$ and $R_2$ are independently hydrogen
or α-methylbutyric acid or isobutyric acid,

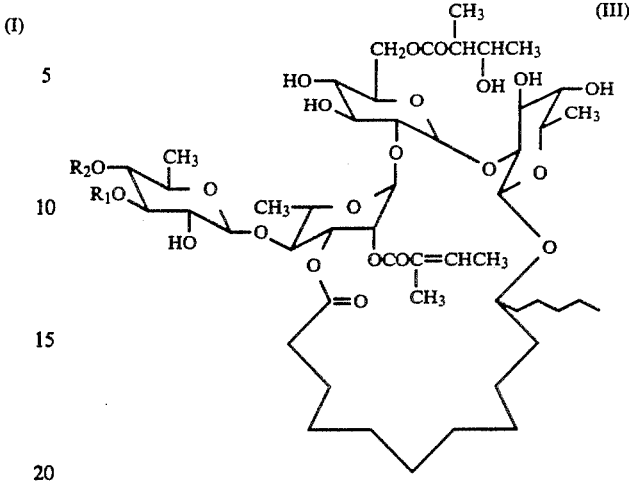
(III)

wherein $R_1$ is hydrogen or isobutyric acid and
$R_2$ is hydrogen, α-methylbutyric acid, isobutyric
acid or nilic acid, and (3) a magnolol derivative represented by the formula

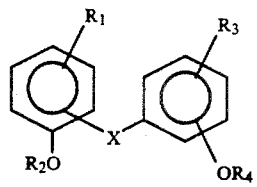

in which each of $R_1$ and $R_3$ represents hydrogen,
halogen, alkyl of 1 to 6 carbon atoms which may
have an oxygen functional group, or allyl, each
of $R_2$ and $R_4$ represents hydrogen, alkyl of 1 to 4
carbon atoms, acyl or allyl, and X represents
oxygen, sulfur or a linkage bond, and (B) an ionophore antibiotic having anticoccidiosis
activity selected from the group consisting of monensin, naracin, salinomycin, lasalocid, carriomycin, maduramicin, a pharmacologically acceptable
salt of such antibiotics and a pharmacologically
acceptable ester of such antibiotics, the ratio of the
plant component (A) to ionophore antibiotic (B)
being such that in a feed composition containing
the combination in which said ionophore antibiotic
is employed in a concentration of from ¼ to 1 times
the recommended concentration thereof, the plant
component is present in an amount of from 0.1 to
1.5% by weight of said feed composition.

9. A pharmaceutical composition for use in the prophylaxis or treatment of coccidiosis which comprises an
anticoccidially effective amount of a combination of (A) a plant component having anticoccidiosis activity
containing a member selected from the group consisting of (1) a condensed tannin represented by the formula

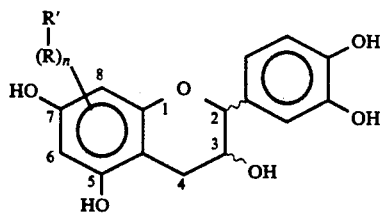
(I)

wherein
R is

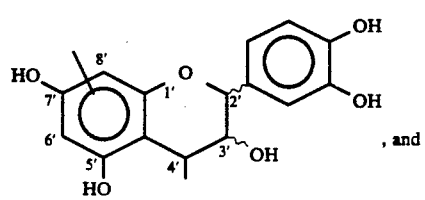
, and

R' is

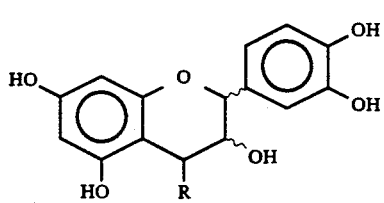

and in which n is an integer of 1 to 15, the 4' position of R is bound to the 6 position or the 8 position of formula (I), R' is bound to the 6' position or the 8' position of R, and when n is an integer of 2 to 15, the 4' position of R is bound to the 6' position or the 8' position of R (2) a resin glycoside represented by formula (II) or (III):

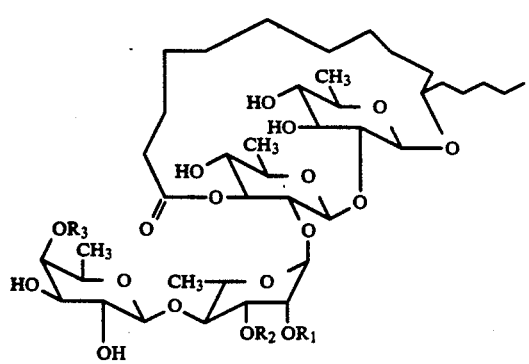
(II)

wherein $R_1$ and $R_2$ are independently hydrogen or α-methylbutyric acid or isobutyric acid,

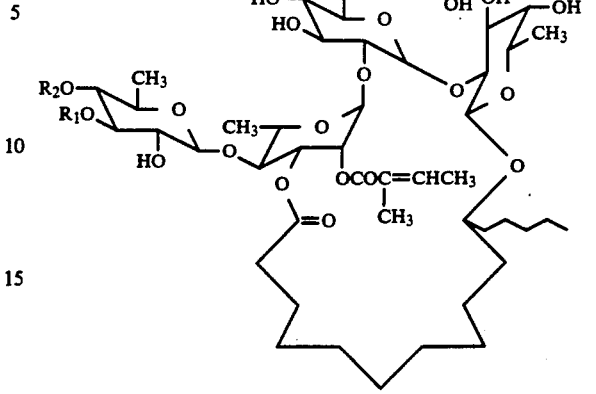
(III)

wherein $R_1$ is hydrogen or isobutyric acid and $R_2$ is hydrogen, α-methylbutyric acid, isobutyric acid or nilic acid, and (3) a magnolol derivative represented by the formula

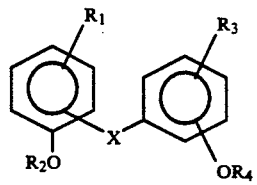

in which each of $R_1$ and $R_3$ represents hydrogen, halogen, alkyl of 1 to 6 carbon atoms which may have an oxygen functional group, or allyl, each of $R_2$ and $R_4$ represents hydrogen, alkyl of 1 to 4 carbon atoms, acyl or allyl, and X represents oxygen, sulfur or a linkage bond, and (B) an ionophore antibiotic having anticoccidiosis activity selected from the group consisting of monensin, naracin, salinomycin, lasalocid, carriomycin, maduramicin, a pharmacologically acceptable salt of such antibiotics and a pharmacologically acceptable ester of such antibiotics, the ratio of the plant component (A) to ionophore antibiotic (B) being such that in a feed composition containing the combination in which said ionophore antibiotic is employed in a concentration of from ¼ to 1 times the recommended concentration thereof, the plant component is present in an amount of from 0.01 to 1.5% by weight of said feed composition and a pharmaceutically acceptable carrier therefor.

10. A composition according to claim 9, wherein the plant component is Rhizophoraceae bark and the ionophore antibiotic is monensin.

11. A composition according to claim 9, which is in the form of an orally administerable feed comprising both the plant component and the ionophore antibiotic.

12. A composition according to claim 11, which is produced by incorporating 0.01 to 1.5% by weight of a purified component (A) having anticoccidial activity to a feed containing the effective amount of an ionophore antibiotic.

13. A composition according to claim 12, wherein the purified component (A) is incorporated in the feed in an amount of 0.01 to 1.0% by weight based on the feed.

14. A composition according to claim 11, which is produced by incorporating 0.01 to 5.0% by weight of an unpurified component (A) having anticoccidial activity in a feed containing an effective amount of the ionophore antibiotic.

15. A composition according to claim 14, wherein the unpurified component (A) is incorporated in the feed in an amount of 0.01 to 2.0% by weight based on the feed.

* * * * *